(12) United States Patent
Inui et al.

(10) Patent No.: US 10,543,356 B2
(45) Date of Patent: Jan. 28, 2020

(54) PAIN SENSORY NERVE STIMULATION APPARATUS

(75) Inventors: Koji Inui, Aichi (JP); Yasuyuki Takeshima, Aichi (JP); Jun Motogi, Tokyo (JP); Yoshinobu Ono, Tokyo (JP); Takeshi Kojima, Tokyo (JP); Ryosuke Ushijima, Tokyo (JP); Katsumi Nakaichi, Tokyo (JP); Kazuwa Shibuya, Tokyo (JP)

(73) Assignees: INTER-UNIVERSITY RESEARCH INSTITUTE CORPORATION, Tokyo (JP); NIHON KOHDEN CORPORATION, Tokyo (JP)

( * ) Notice: Subject to any disclaimer, the term of this patent is extended or adjusted under 35 U.S.C. 154(b) by 460 days.

(21) Appl. No.: 13/023,623

(22) Filed: Feb. 9, 2011

(65) Prior Publication Data

US 2011/0196256 A1 Aug. 11, 2011

(30) Foreign Application Priority Data

Feb. 9, 2010 (JP) .................................. 2010-026278

(51) Int. Cl.
- *A61N 1/04* (2006.01)
- *A61N 1/36* (2006.01)
- *A61B 5/00* (2006.01)

(52) U.S. Cl.
CPC .......... *A61N 1/0456* (2013.01); *A61B 5/4824* (2013.01); *A61N 1/0472* (2013.01); *A61N 1/36021* (2013.01)

(58) Field of Classification Search
CPC ...... A61B 5/05; A61B 5/4893; A61N 1/36014

USPC ...... 600/554, 557; 607/9, 22, 23, 46, 63, 68, 607/74
See application file for complete search history.

(56) References Cited

U.S. PATENT DOCUMENTS

| | | | |
|---|---|---|---|
| 2,771,554 A | | 11/1956 | Gratzl |
| 5,097,833 A | * | 3/1992 | Campos .......................... 607/68 |
| 5,806,522 A | * | 9/1998 | Katims .......................... 600/554 |

(Continued)

FOREIGN PATENT DOCUMENTS

| | | |
|---|---|---|
| CN | 101578065 A | 11/2009 |
| EP | 2 174 589 A1 | 4/2010 |

(Continued)

OTHER PUBLICATIONS

English translation to WO2006/059430, dated Nov. 17, 2011.*

(Continued)

*Primary Examiner* — Daniel L Cerioni
(74) *Attorney, Agent, or Firm* — Sughrue Mion, PLLC

(57) ABSTRACT

A pain sensory nerve stimulation apparatus includes: an electrode portion including: a first electrode, a tip end of which is adapted to be inserted into a skin; and at lease one second electrode which is disposed in a circumference of the first electrode without being electrically conductive with the first electrode, and which is adapted to be in contact with a skin; and a stimulation signal supplying unit, supplying a bipolar stimulation signal between the first electrode and the second electrode, the bipolar stimulation signal including a first waveform signal and a second waveform, the first waveform which is convex in a negative direction in the first electrode, the second waveform signal which is convex in a positive direction in the first electrode.

20 Claims, 9 Drawing Sheets

(56) References Cited

U.S. PATENT DOCUMENTS

| | | | |
|---|---|---|---|
| 5,861,013 A * | 1/1999 | Peck | A61N 1/371 |
| | | | 607/28 |
| 8,290,585 B2 * | 10/2012 | Mower | 607/9 |
| 2002/0099413 A1 | 7/2002 | Mower | |
| 2007/0016264 A1 * | 1/2007 | Falci | 607/46 |
| 2010/0036280 A1 | 2/2010 | Ballegaard et al. | |
| 2010/0094378 A1 | 4/2010 | Inui et al. | |

FOREIGN PATENT DOCUMENTS

| | | |
|---|---|---|
| JP | 3543097 B2 | 4/2004 |
| JP | 2006/059430 T | 6/2006 |
| WO | 2005046787 A1 | 5/2005 |
| WO | 2006/059430 A1 | 6/2006 |

OTHER PUBLICATIONS

Office Action issued by the Japanese Patent Office dated Jun. 27, 2013 in corresponding Application No. 2010-026278.
Communication dated May 5, 2014 issued by the State Intellectual Property Office of the People's Republic of China in counterpart Chinese Patent Application No. 201110035314.1.
Office Action, Issued by the European Patent Office, dated Sep. 10, 2014, in counterpart European Application No. 11153842.7.
Office Action dated Apr. 3, 2015, issued by the State Intellectual Property Office of P.R. China in counterpart Chinese Application No. 201110035314.1.
Communication dated Feb. 7, 2019, issued by the European Patent Office in counterpart European Patent Application No. 11153842.7.

* cited by examiner

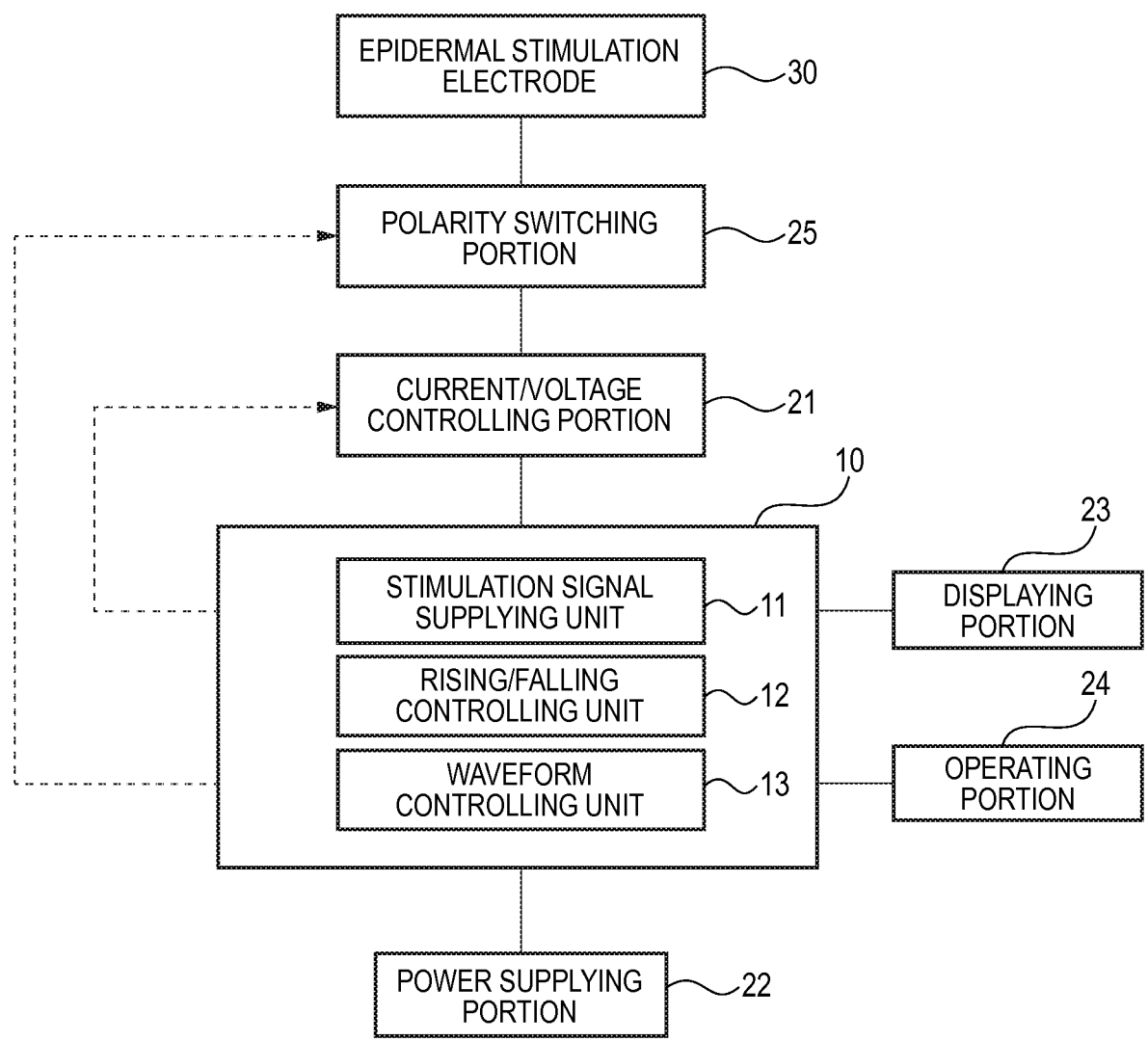

PAIN SENSORY NERVE STIMULATION APPARATUS

BACKGROUND OF THE INVENTION

The present invention relates to a pain sensory nerve stimulation apparatus which, with respect to the primary pain sense produced by stimulation of Aδ fibers, and the secondary pain sense produced by stimulation of C fibers, can perform only stimulation of C fiber.

In order to stimulate only the pain sense by electrical stimulation, an electrode disclosed in Patent Reference 1 has been developed. According to the electrode, it is possible to stimulate Aδ fibers (see FIG. 3 of Patent Reference 1).

By contrast, in order to early detect a disorder of peripheral nerve which is one of the three major complications of diabetes, a method in which only C fibers are stimulated and a reaction to the stimulation is checked is highly requested. This is based on that C fibers have a thickness of 0.4 to 1.2 μm, Aδ fibers have a thickness of 2 to 5 μm, Aβ fibers which are connected to mechanoreceptors of the tactile sense, the pressure sense, and the like have a thickness of 5 to 12 μm, and a nervous disorder begins from small fibers. When it possible to stimulate C fibers which are smaller than Aδ fibers that can be stimulated in Patent Reference 1, therefore, development of a nervous disorder can be known more early, thereby largely contributing to knowing of progression of and adequate control of a diabetic nervous disorder. In a related-art technique of stimulating only C fibers, a laser apparatus is used. In the case where a laser apparatus is used, however, large-scale testing equipment and facility are required, and the size, cost, and complexity of the apparatus are increased to cause a problem of versatility. The accuracy of C fiber stimulation by laser light has not yet reached to a satisfactory level, and the probability of C fiber stimulation is lower. Therefore, a laser apparatus has not been used in a clinical application.

Also in Patent Reference 1, when stimulation is applied while a needle terminal of the stimulation electrode is set as a negative pole and the surrounding electrode is set as a positive pole, it is possible to selectively stimulate A6 fibers, but C fibers cannot be selectively stimulated.

In the field of the art, a related-art technique in which electrical stimulation of the negative polarity is applied to a stimulation object electrode attached to a desired stimulation portion, and the positive polarity is applied to an end electrode is employed because excitation of peripheral nerves is generated immediately below a stimulation electrode of the negative polarity. Also Patent Reference 1 describes that stimulation is applied while the needle electrode of the stimulation electrode is set as a negative pole and the surrounding electrode is set as a positive pole, so that Aδ fibers can be selectively stimulated. However, in the field, even when the electrical polarity is inverted, the inversion exerts no effect or influence on nerve stimulation from the skin surface which is used in a measurement of the somatosensory evoked potential SEP (see FIG. 9).

Patent Reference 2 discloses a related-art apparatus which automatically measures in an electrophysiologic or quantitative manner the electrical current perceptive threshold and the algestic tolerant threshold. In the to related-art apparatus, stimulation is applied by using a sine wave, and C fibers, Aδ fibers, and Aβ fibers are most responsive to stimulation of frequencies of 5 Hz, 250 Hz, and 2,000 Hz, respectively. Patent Reference 2 does not provide a technique in which C fibers, Aδ fibers, and Aβ fibers can be independently stimulated. In the related-art apparatus, stimulation due to a sine wave is required. Therefore, the apparatus is complicated in structure for producing and controlling stimulation, as compared with the case where stimulation is applied by a pulse wave which is typified by a square wave.

The technique disclosed in Patent Reference 2 uses a surface electrode, and hence the stimulation intensity to be applied is larger than the case where an electrode is inserted into the skin. In stimulation of small fibers such as C fibers, namely, there is a large possibility that also other nerve fibers such as the tactile sense are stimulated. Therefore, it is considered that selective stimulation of only C fibers is difficult.

Patent Reference 3 discloses a related-art technique in which specific tactile sensory receptors are selectively stimulated by using a surface electrode and without performing stimulation on the pain sense. This technique is effective in stimulating the tactile sense. Since the surface electrode is used, however, the stimulation intensity is as large as about 2 mA. Furthermore, Aδ fibers and C fibers which relate to the pain sense are small fibers, and hence stimulation is hardly performed. In the related-art technique disclosed in Patent Reference 3, therefore, it is impossible to selectively stimulate Aδ fibers and C fibers. The related-art technique disclosed in Patent Reference 3 has a further problem in that a complex process such as a weighted change is required in selective stimulation of receptors.

In electrical stimulation, excitation is more easily caused in the sequence of Aβ fibers, Aδ fibers, and C fibers. Namely, electrical stimulation is more easily performed on larger medullated fibers having an axial fiber, and excitation due to electrical stimulation most hardly occurs in C fibers which are small fibers, and which are nonmedullated fibers. Therefore, stimulation in which only C fibers are selectively stimulated without stimulating other fibers is very difficult.

[Patent Reference 1] JP-T-2006-59430
[Patent Reference 2] U.S. Pat. No. 5,806,522
[Patent Reference 3] Japanese Patent No. 3,543,097

SUMMARY

It is therefore an object of the invention to provide a simple pain sensory nerve stimulation apparatus which can accurately stimulate only C fibers by electrical stimulation with a very high probability and irrespective of the skill of the operator and to provide a pain sensory nerve stimulation apparatus which can independently stimulate C fibers in an adequate manner according to individual differences.

In order to achieve the object, according to the invention, there is provided a pain sensory nerve stimulation apparatus comprising: an electrode portion including: a first electrode, a tip end of which is adapted to be inserted into a skin; and at lease one second electrode which is disposed in a circumference of the first electrode without being electrically conductive with the first electrode, and which is adapted to be in contact with a skin; and a stimulation signal supplying unit, supplying a bipolar stimulation signal between the first electrode and the second electrode, the bipolar stimulation signal including a first waveform signal and a second waveform, the first waveform which is convex in a negative direction in the first electrode, the second waveform signal which is convex in a positive direction in the first electrode.

The pain sensory nerve stimulation apparatus may further include: a rising/falling controlling unit, changing at least one of a rising time and a falling time of each of the first and second waveform signals.

At least one of rising and falling of each of the first and second waveform signals may be changed so as to have a rectilinear inclined shape.

At least one of rising and falling of each of the first and second waveform signals may be changed so as to have an exponential shape.

The pain sensory nerve stimulation apparatus may further include: a stimulation intensity controlling unit, changing at least one of a voltage and a current of each of the first and second waveform signals.

The pain sensory nerve stimulation apparatus may further include: a waveform controlling unit, changing at least one of a waveform duration, waveform interval, and waveform number of each of the first and second waveform signals.

In the bipolar stimulation signal, the second waveform signal may be supplied after the first waveform signal is supplied, and the first and second waveform signals may be connected to each other.

A peak value of the first waveform signal may be different from a peak value of the second waveform signal.

A peak value of the second waveform signal may be higher than a peak value of the first waveform signal.

The bipolar stimulation signal may have a waveform duration of 0.1 to 100 ms.

A peak value of the second waveform signal may be five times or more a peak value of the first waveform signal.

Rising and falling times of the first waveform signal may be equal to rising and falling times of the second waveform signal.

The second electrode may be annularly disposed in the circumference of the first electrode.

The pain sensory nerve stimulation apparatus may include a plurality of the electrode portion.

The stimulation signal supplying unit may be adapted to successively supply a plurality of times the bipolar stimulation signal.

BRIEF DESCRIPTION OF THE DRAWINGS

FIG. 1 is a block diagram showing the configuration of an embodiment of the pain sensory nerve stimulation apparatus of the invention.

DETAILED DESCRIPTION OF EMBODIMENTS

Figure 2A:
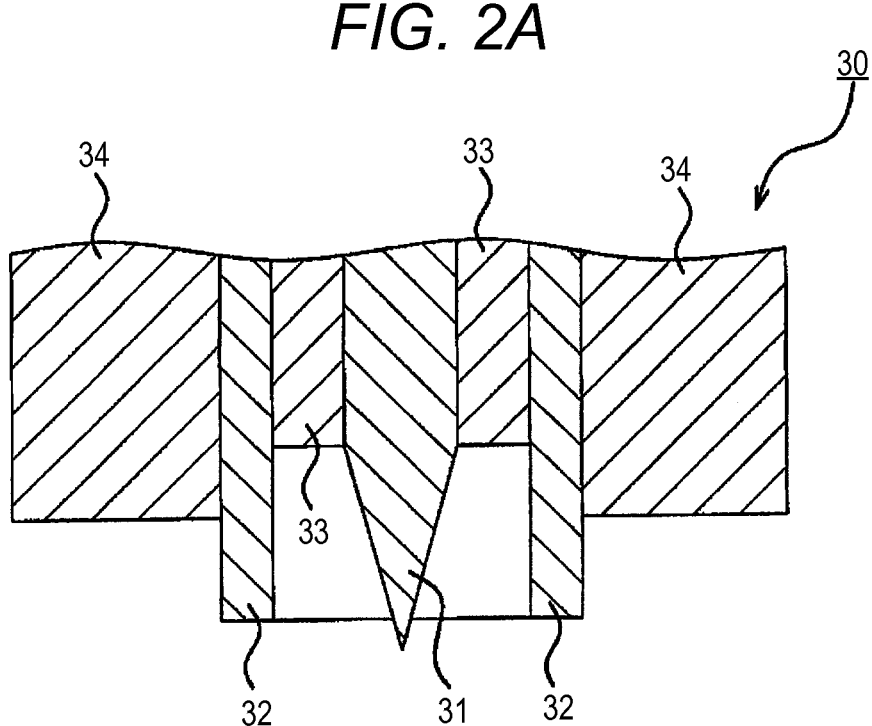
FIG. 2A is a sectional view showing the configuration of electrodes used in the embodiment of the pain sensory nerve stimulation apparatus of the invention.

Hereinafter, the pain sensory nerve stimulation apparatus of the invention and examples of a method of using the apparatus will be described with reference to the accompanying drawings. In the pain sensory nerve stimulation apparatus, as shown in FIG. 1, a current/voltage controlling portion 21, a power supplying portion 22, a displaying portion 23, and an operating portion 24 are connected to a signal generation body unit 10. A polarity switching portion 25 is connected to the current/voltage controlling portion 21, and an epidermal stimulation electrode portion 30 is connected to the polarity switching portion 25.

Figure 2B:
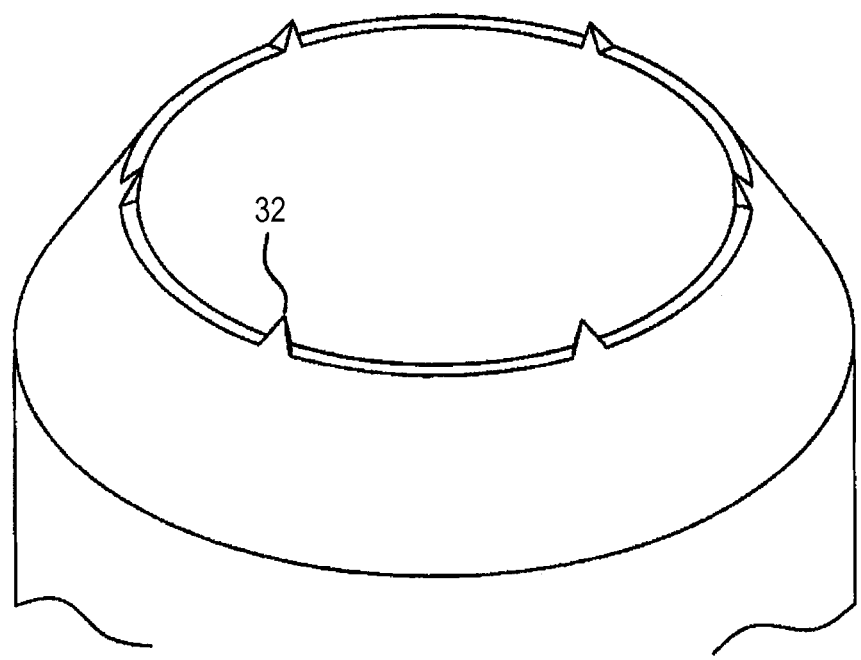
FIG. 2B is a perspective view showing an example of the electrodes used in the embodiment of the pain sensory nerve stimulation apparatus of the invention.

The epidermal stimulation electrode portion 30 is structured in a substantially same manner as the electrode disclosed in Patent Reference 1. FIG. 2A is a sectional view of the portion. The epidermal stimulation electrode portion 30 includes: a needle electrode 31 functioning as a first electrode in which the tip end has a shape that allows the tip end to be slightly inserted into the skin (for example, from the skin surface to the papilla); and a contact electrode 32 functioning as a second electrode which is to be used while being in contact with the skin. As seen from FIG. 2, the needle electrode 31 is projected with respect to the contact electrode 32. The tip end of the needle electrode 31 is not always necessary to be pointed, and may have a spherical or rod-like shape. The contact electrode 32 may have a cylindrical shape which surrounds the needle electrode 31 while being centered at the needle electrode 31, or alternatively a plurality of contact electrodes 32 may be cylindrically placed so as to be centered at the needle electrode 31. The contact electrode has an inner diameter of, for example, 1 mm. As shown in FIG. 2B, a part of the contact electrode 32 may have a sharp shape which enables the part to be slightly inserted into the skin.

A spacer 33 configured by an insulating material may be embedded in the gap between the contact electrode 32 and the needle electrode 31. An external fitting portion 34 which has a columnar shape using the contact electrode 32 as a core, and which is formed by an insulating material is disposed in the circumference of the contact electrode 32.

The signal generation body unit 10 is configured by an analog/digital microprocessor, and includes a stimulation signal supplying unit 11 which generates and supplies a stimulation signal, a rising/falling controlling unit 12, and a waveform controlling unit 13. The stimulation signal supplying unit 11 supplies a bipolar stimulation signal formed by a combination of a first waveform signal P1 which is convex in the negative direction in the needle electrode 31, and a second waveform signal P2 which is convex in the positive direction in the needle electrode 31, between the needle electrode 31 and the contact electrode 32. In the embodiment, the waveforms of the signals are configured so that the second waveform signal P2 has a peak value different from that of the first waveform signal P1. Specifically, for example, the bipolar stimulation signal has the waveform shown in an enlarged view of FIG. 3.

Figure 4:
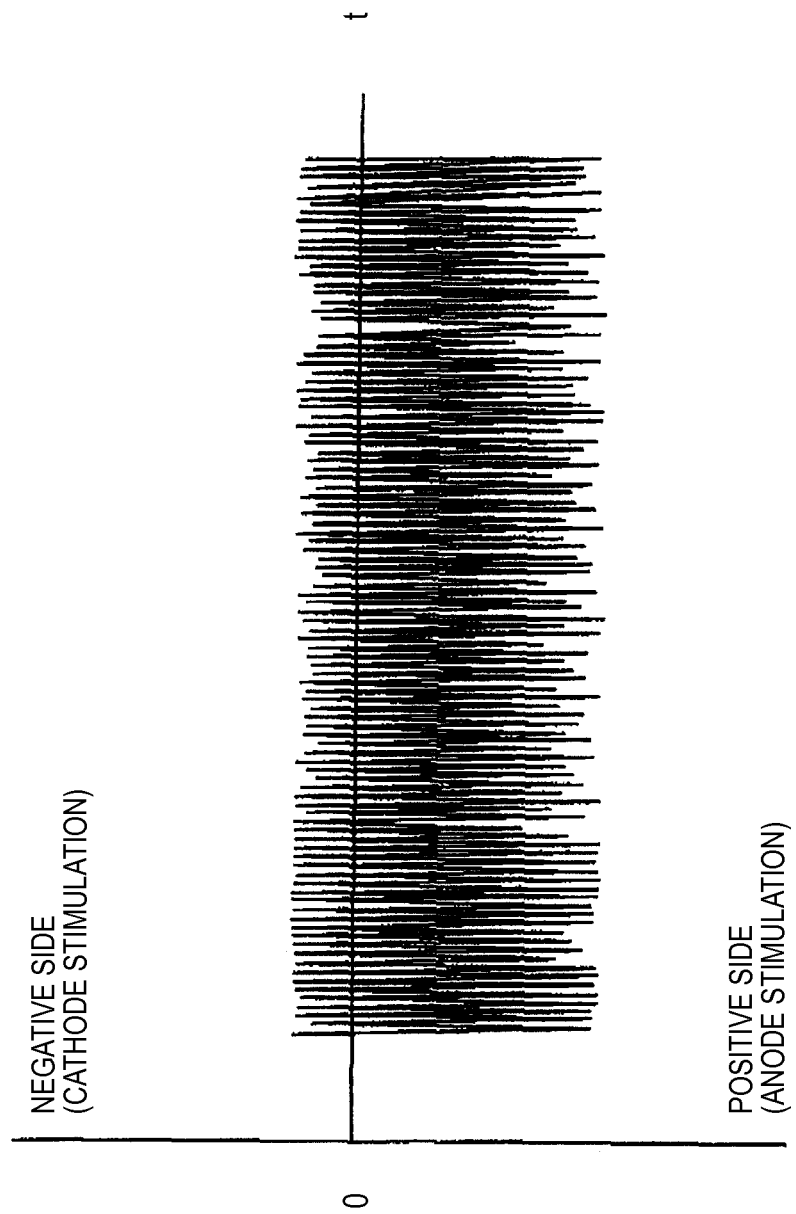
FIG. 4 is a view showing the stimulation signal shown in FIG. 3 with reducing the time scale.
Figure 5:
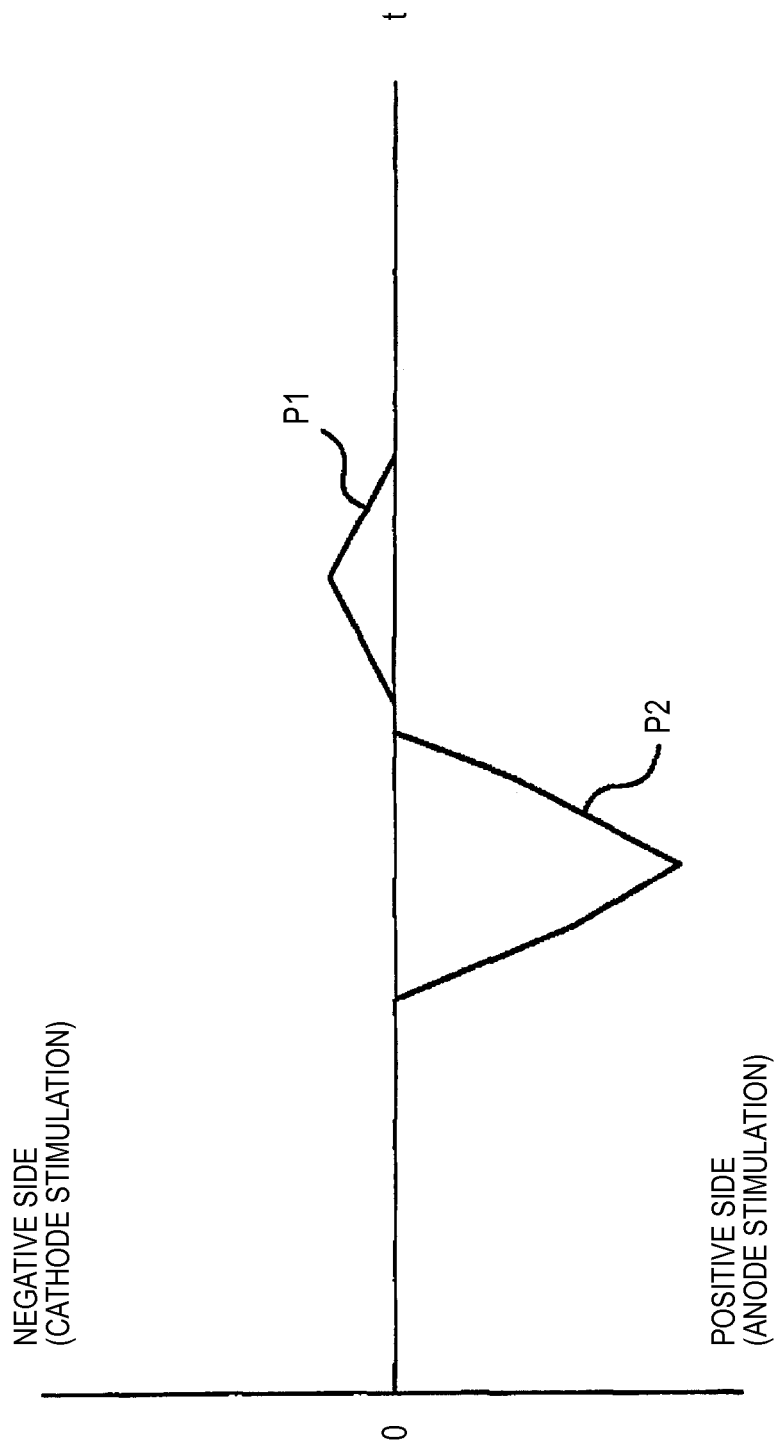
FIG. 5 is a view illustrating first and second waveform signals constituting the stimulation signal which is supplied in the embodiment of the pain sensory nerve stimulation apparatus of the invention.

As shown in FIG. 4, the stimulation signal supplying unit 11 can successively supply the bipolar stimulation signal a plurality of times (for example, 100 times). When the stimulation signal is decomposed, as shown in FIG. 5, the signal is configured by combining a sawtooth wave which is the first waveform signal P1, with another sawtooth wave which is the second waveform signal P2. The bipolar stimulation signal is formed as a pulse-like stimulation signal by alternately successively (without no interval between the waveform signals) arranging the first waveform signal P1 and the second waveform signal P2.

In the stimulation signal supplied from the stimulation signal supplying unit 11, preferably, the peak value of the first waveform signal P1 is different from that of the second waveform signal P2. As far as the convex directions of the waveform signals are opposite to each other, the stimulation signal may be configured by any of: a waveform signal in which inclined rising and falling portions are linear as shown in column a of FIG. 6; that in which the portions are exponential as shown in column b; and that in which the portions are gently upward convex (a parabolic shape, or the like). Alternatively, the stimulation signal may be a usual pulse signal.

In the case where the first waveform signal P1 and the second waveform signal P2 are combined with each other, waveforms which are convex in the same direction may be continued five times at the maximum, or a combination in which waveforms of the first waveform signal P1 and those of the second waveform signal P2 are not regularly arranged in the same number may be used. Intervals (flat portions) may be disposed between waveforms of the first waveform signal P1 and those of the second waveform signal P2.

Figure 6:
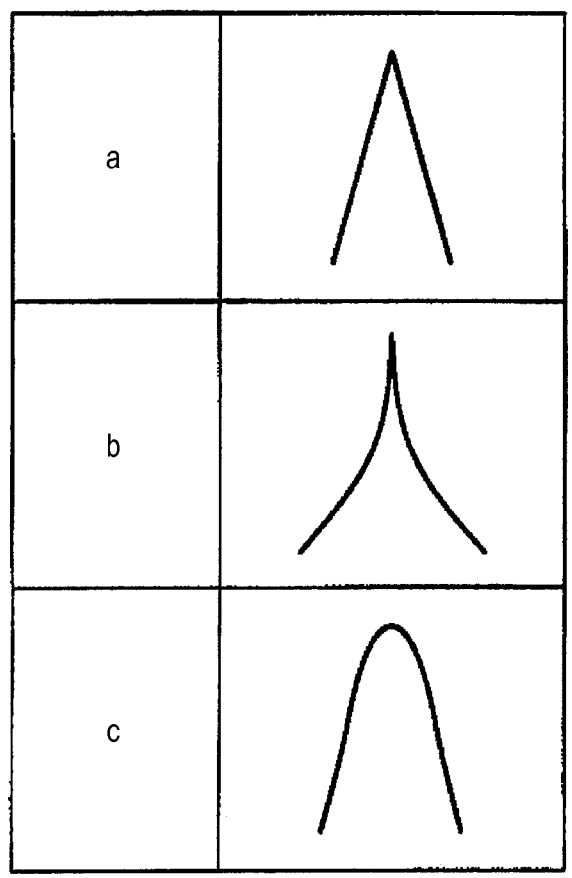
FIG. 6 is a view illustrating various waveforms of the first and second waveform signals constituting the stimulation signal which is supplied in the embodiment of the pain sensory nerve stimulation apparatus of the invention.

The rising/falling controlling unit 12 changes at least one of the rising and falling times of waveform signals of the stimulation signal supplied from the stimulation signal supplying unit 11. The operating portion 24 constituting an instruction inputting portion may be configured by dials, buttons, a keyboard, a touch panel, or the like, and includes a rising/falling time instructing unit. The rising/falling time instructing unit can give an instruction input for changing the stimulation signal to a signal configured by a combination of waveform signals having desired rising and falling times, to the rising/falling controlling unit 12. Furthermore, the rising/falling controlling unit 12 can select either of a rectilinear mode where the rise and fall of each waveform signal have rectilinearly rising and falling shapes, and an exponential mode where the rise and fall of each waveform signal have exponentially rising and falling shapes, so that the stimulation signal can be produced in which waveform signals having one shape that is selected from a plurality of shapes such as shown in FIG. 6 described above are combined with each other while setting upward convex and downward convex.

Figure 7:
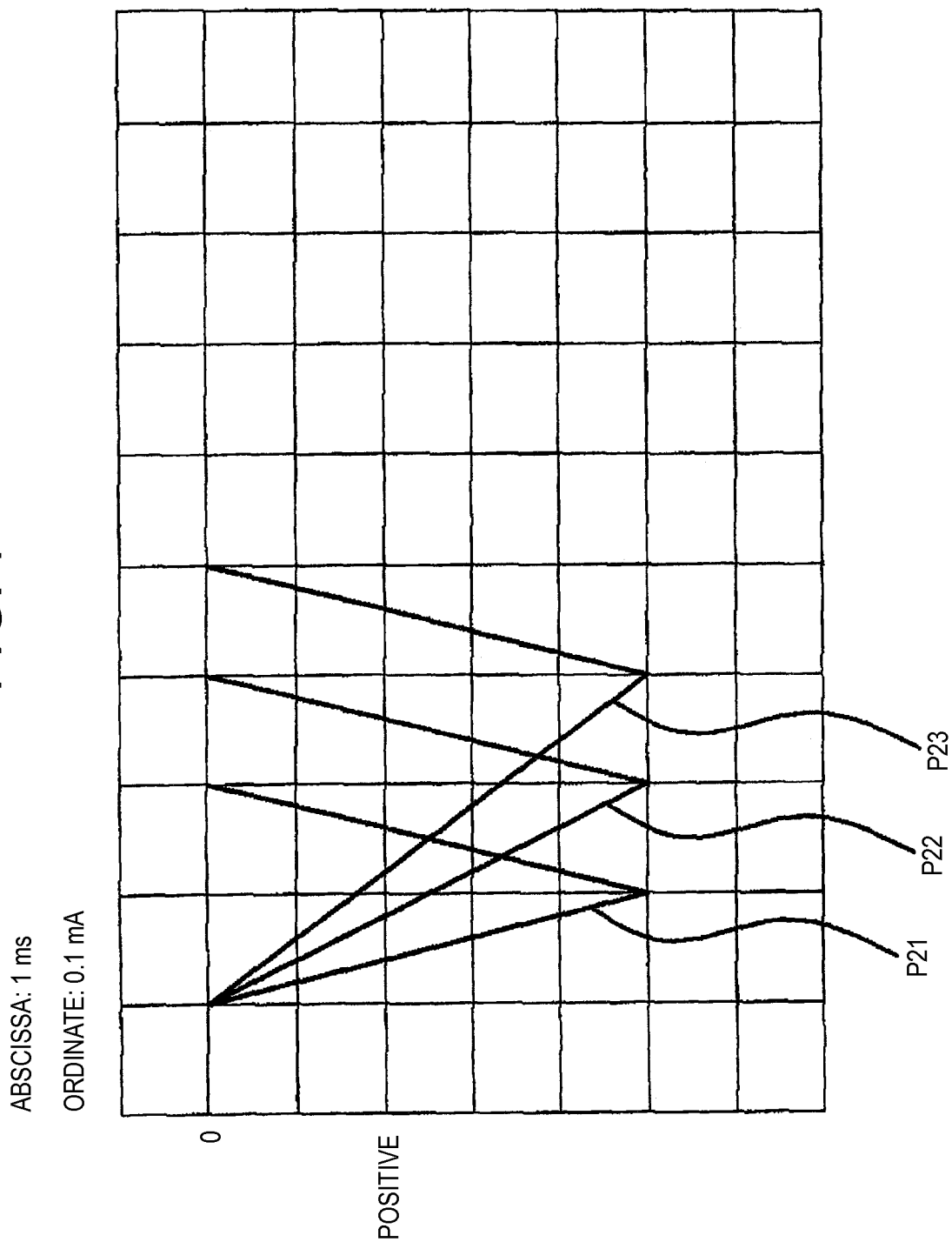
FIG. 7 is a view showing waveforms of stimulation signals which are supplied in the embodiment of the pain sensory nerve stimulation apparatus of the invention, and in which the rising and falling times are made different.

In the instruction input from the rising/falling time instructing unit, the rising time and the falling time can be designated. As the rising time and the falling time, for example, a desired value can be selected from 0 ms to about 15 ms. FIG. 7 shows three kinds of second waveform signals P21 to P23 which are in the rectilinear mode, in which their falling times are 1 ms, 2 ms, and 3 ms, respectively, and which are convex in the positive direction.

The waveform controlling unit 13 disposed in the signal generation body unit 10 changes the waveform duration, waveform interval, and waveform number of the stimulation signal supplied from the stimulation signal supplying unit 11. The operating portion 24 includes a waveform instructing unit. The waveform instructing unit can give instructions for causing the waveform controlling unit 13 to change the stimulation signal to a signal configured by waveforms of a desired waveform duration, waveform interval, and waveform number.

The waveform duration, the waveform interval, and the waveform number are selected. The waveform duration can be selected from 0.5 to 30 ms in increments of, for example, 0.1 ms, the waveform interval can be selected from 1 to 100 ms in increments of, for example, 1 ms, and the waveform number can be selected in increments of, for example, 1.

The current/voltage controlling portion 21 connected to the signal generation body unit 10 is a stimulation intensity controlling unit for changing at least one of the voltage and current of each of the first waveform signal P1 and second waveform signal P2 supplied from the stimulation signal supplying unit 11. The voltage and the current correspond to the peak value of the first waveform signal P1 or the second waveform signal P2. The operating portion 24 includes a stimulation intensity instructing unit. The stimulation intensity instructing unit can give instructions for causing the current/voltage controlling portion 21 functioning as the stimulation intensity controlling unit, to change the peak values of the first waveform signal P1 and the second waveform signal P2 to desired currents or voltages.

Figure 8:
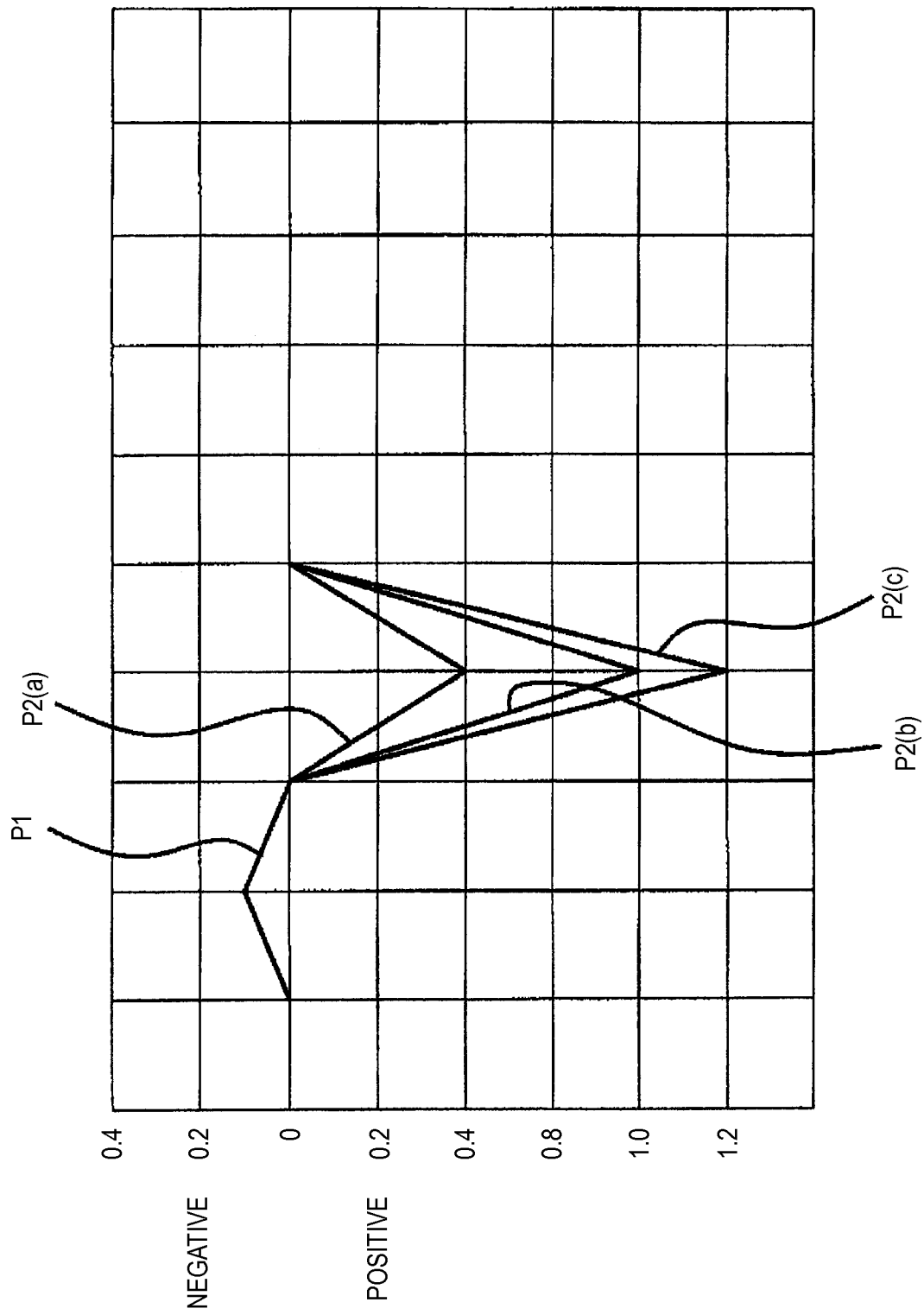
FIG. 8 is a view showing waveforms of stimulation signals which are supplied in the embodiment of the pain sensory nerve stimulation apparatus of the invention, and in which the peak values are made different.
Figure 9:
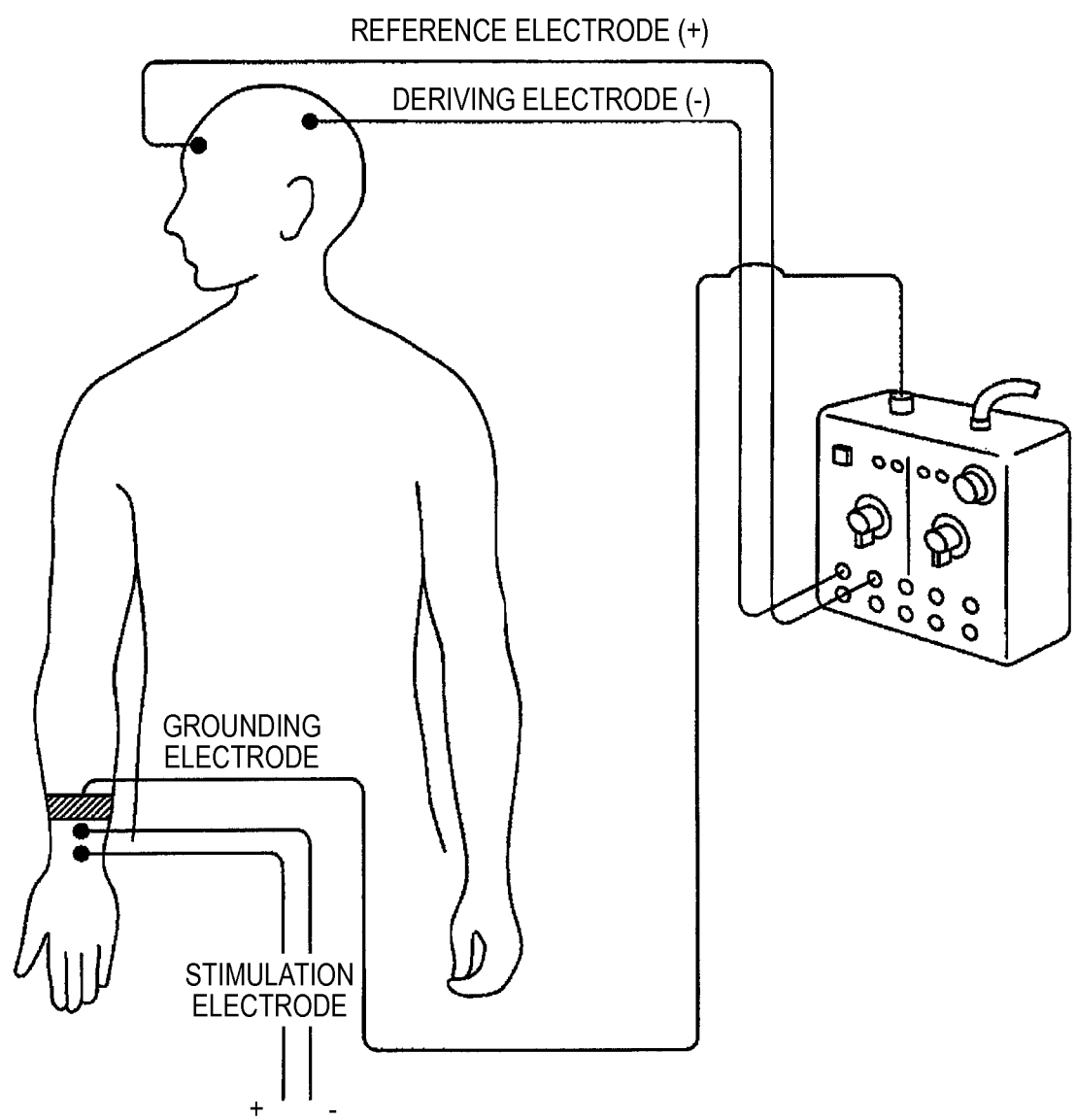
FIG. 9 is a view showing an arrangement of electrodes with respect to a living body in a measurement of the somatosensory evoked potential SEP.

In the case of the current control, for example, the current/voltage controlling portion is configured so that the current can be raised from 0.0 mA at 0.01 mA intervals to a predetermined value (also can be lowered from a desired value). After the needle electrode 31 and the contact electrode 32 are attached, the inter-electrode impedance is seemed to be constant. Therefore, the portion may be configured so that the voltage can be raised from a predetermined value (for example, 0 V) at 0.2 V intervals to another predetermined value (also can be lowered from a desired value). Alternatively, a configuration in which the peak value of the first waveform signal P1 can be input, and a multiplication factor (actually, a fraction) of the peak value of the second waveform signal P2 with respect to the first waveform signal P1 can be input may be employed, or by contrast that in which the peak value of the second waveform signal P2 can be input, and a multiplication factor of the peak value of the first waveform signal P1 with respect to the second waveform signal P2 can be input may be employed. The example of FIG. 8 shows waveform signals P2(a), P2(b), P2(b) in which the peak values of the second waveform signals P2 are set respectively to four, eight, and ten times in the positive side with respect to the first waveform signal P1 that is 0.1 mA in the negative side.

Figure 3:
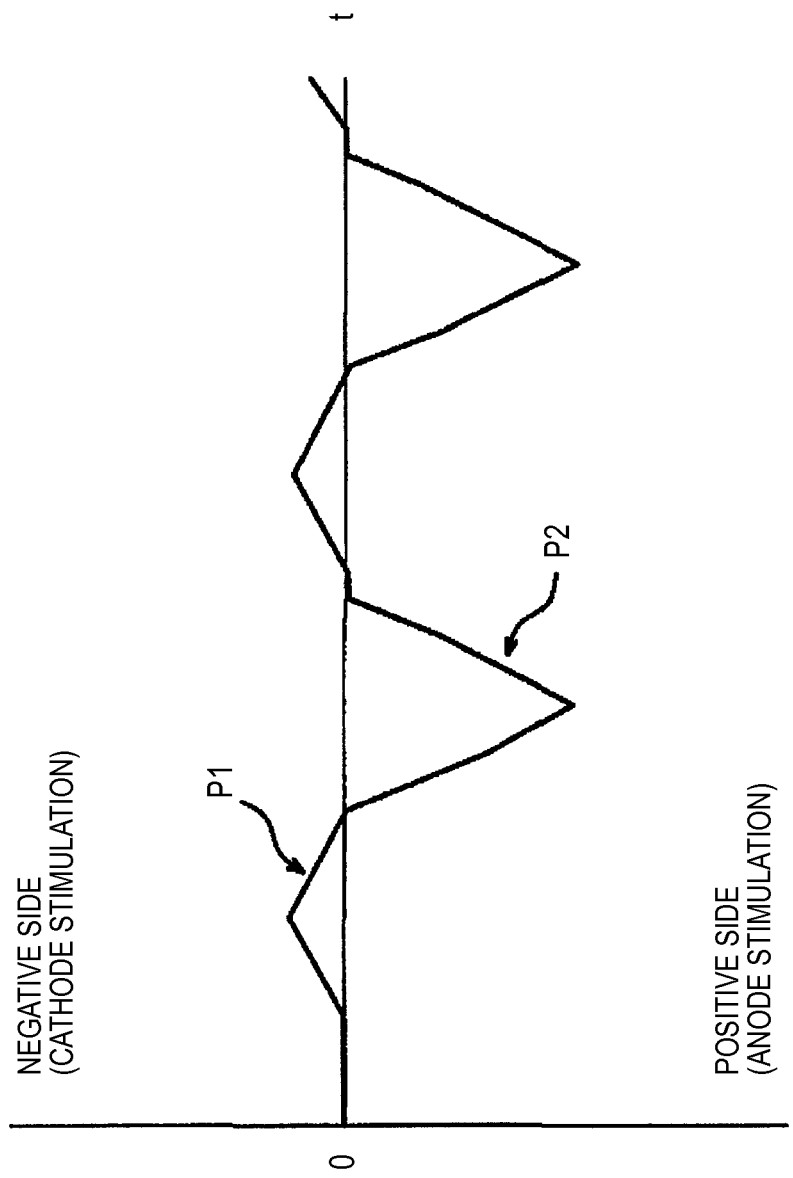
FIG. 3 is a view showing waveforms of a stimulation signal which is supplied in the embodiment of the pain sensory nerve stimulation apparatus of the invention.

The polarity switching portion 25 connected to the current/voltage controlling portion 21 functions as an electrical polarity converting unit for converting between the electrical polarity of the needle electrode 31 and that of the contact electrode 32. The operating portion 24 includes a polarity conversion instructing unit. The polarity conversion instructing unit can give instructions for causing the polarity switching portion 25 functioning as the electrical polarity converting unit to convert the electrical polarity. According to the configuration, the electrical polarity of the needle electrode 31 may be set as the positive pole, and that of the contact electrode 32 may be set as the negative pole. When the stimulation signal of FIG. 3 or 4 is supplied in this state, a bipolar stimulation signal configured by a combination of a first inverted waveform signal in which, in the needle electrode 31, the first waveform signal P1 is convex in the negative direction, and a second inverted waveform signal in which, in the needle electrode 31, the second waveform signal P2 is convex in the positive direction is supplied. By contrast, the electrical polarity of the needle electrode 31 may be set as the negative pole, and that of the contact electrode 32 may be set as the positive pole. In this case, when the stimulation signal of FIG. 3 or 4 is supplied, a bipolar stimulation signal configured by a combination of a first inverted waveform signal in which, in the needle electrode 31, the first waveform signal P1 is convex in the positive direction, and a second inverted waveform signal in which, in the needle electrode 31, the second waveform signal P2 is convex in the negative direction is supplied.

Character information produced by the generation body unit 10, such as the present stimulation intensity (mA), the rising times, falling times, waveform durations, waveform intervals, and waveform numbers of the waveform signals, and the polarities of the electrodes can be displayed on the displaying portion 23.

The thus configured pain sensory nerve stimulation apparatus is used in the following manner. First, the epidermal stimulation electrode portion 30 is contacted with the skin in the test area of the subject, and fixed thereto so that the needle electrode 31 is inserted into the skin. At this time, the needle electrode 31 is inserted into the skin by a depth of about 0.01 to 0.3 mm. Next, the operating portion 24 is operated so as to supply the stimulation signal of FIG. 3 or 4. In the first waveform signal P1, then, the needle electrode 31 is in the negative side, so that the cathode stimulation is performed, and, in the second waveform signal P2, the needle electrode 31 is in the positive side, so that the anode stimulation is performed.

The operating portion 24 is further operated so as to cause: the rising/falling time instructing unit to give an instruction input for causing the rising/falling controlling unit 12 to change the stimulation signal to have desired rising and falling times; the waveform instructing unit to give instructions for causing the waveform controlling unit 13 to change the stimulation signal to have a desired waveform duration, waveform interval, and waveform number; and the stimulation intensity instructing unit to give instructions for causing the current/voltage controlling portion 21 functioning as the stimulation intensity controlling unit, to change the stimulation signal to have a desired current or voltage. From the display on the displaying portion 23, it is checked that desired settings are performed by the operating portion 24, and an operation of starting stimulation is then performed.

As described above, the stimulation signal such as shown FIG. 3 or 4 is applied between the needle electrode 31 and the contact electrode 32 to perform stimulation. In this state, the operating portion 24 is operated so as to gradually increase the current value (or the voltage value) until the subject feels pain. Alternatively, measurement may be conducted while the rising and falling times are changed, or while the waveform duration, waveform interval, and waveform number are changed. If the subject has a nervous disorder, this can be determined from a phenomenon that the subject does not feel pain, or that, even the subject feels pain, stimulation of higher intensity is required. Moreover, the epidermal stimulation electrode portion 30 is contacted with the skin in another (or the identical) test area of the subject, so that differences depending on the stimulation position, a difference between right and left body portions, and the like can be checked. When the operating portion 24 is operated so as to convert the electrical polarities of the needle electrode 31 and the contact electrode 32 and then measurements are conducted in the same manner as described above, also knowing of progression of and adequate control of a diabetic nervous disorder can be checked.

In this field, it is said that a C fiber nociceptive receptor relates to steady or burning pain which is typified by inflammation, and an Aδ nociceptive receptor controls sharp pain. When the subject was stimulated by the stimulation apparatus of the invention, the number of the cases where the subject felt steady or burning pain irrespective of the skill of the operator was increased as compared with the related art. This means that, instead of Aδ fibers, C fibers can be accurately stimulated.

In the embodiment, in the case where the peak value of the second waveform signal is five times or more that of the first waveform signal, remarkable results were obtained. In the case where the bipolar stimulation signal was successively supplied a plurality of times, remarkable results were obtained.

In the above-described embodiment, it is a matter of course that a configuration in which a plurality of epidermal stimulation electrode portions 30 are disposed may be employed and used.

According to an aspect of the invention, only C fibers having the thinnest fiber diameter were stimulated by supplying the bipolar stimulation signal formed by the combination of the first waveform signal which is convex in the negative direction in the first electrode, and the second waveform signal which is convex in the positive direction in the first electrode. The first electrode has a needle-like shape, and hence the area contacting with a living body is very smaller than that of the second electrode. Therefore, there is a possibility that C fibers which are thinner than Aδ fibers cannot be adequately excited. This is caused mainly by the fact that smaller fibers have a lower threshold with respect to electrical stimulation. By contrast, C fibers have possibly available physical properties such as that the distribution density is higher than Aδ fibers, that the fibers run perpendicularly to the skin surface, and that the fibers extend to the surface part as compared with ends of mechanoreceptors. According to an aspect of the invention, it was noted that the number of subjects answering that a sense of burning pain which is typified by inflammation is caused is very larger as compared with a case of any of related-art techniques including the technique disclosed in JP-A-2010-088802 which was previously filed by the inventors of the present application, and only C fibers can be stimulated without substantially affecting other nerve fibers. This means that the apparatus of the invention can stimulate only C fibers with a high probability and irrespective of the skill of the operator.

According to an aspect of the invention, the apparatus includes the rising/falling controlling unit for changing at least one of rising and falling times of each of the waveform signal. While at least one of rising and falling times of each of the waveform signal is changed, therefore, the supply of the stimulation signal in which only C fibers having the smallest diameter are stimulated without substantially affecting other nerve fibers can be performed.

According to an aspect of the invention, the apparatus includes the stimulation intensity controlling unit for changing at least one of the voltage and current of the stimulation signal supplied from the stimulation signal supplying unit. Therefore, also Aδ fibers and Aβ fibers which are larger nerve fibers can be stimulated by changing the stimulation intensity.

According to an aspect of the invention when the stimulation intensity is changed, respective nerve fibers can be stimulated in the sequence which is opposite to the excitability sequence (Aβ, Aδ, and C) in the usual electrical stimulation. Particularly, C fibers can be selectively stimulated at a weak stimulation intensity.

According to an aspect of the invention, the apparatus includes the waveform controlling unit for changing the waveform duration, waveform interval, and waveform number of the stimulation signal supplied from the stimulation signal supplying unit. Therefore, a measurement which absorbs individual differences can be performed while searching the waveform duration, waveform interval, and waveform number at which stimulation of C fibers only is enabled.

Even when stimulation is performed on a part of nerve fibers, effects and reactions caused by stimulations are identical with one another. When a plurality of electrode portions are used or the bipolar stimulation signal is successively supplied a plurality of times, therefore, only C fibers can be stimulated with a higher probability and irrespective of the skill of the operator.

What is claimed is:

1. A pain sensory nerve stimulation apparatus comprising:
    an electrode portion including:
        a first electrode, a tip end of which is adapted to be inserted into a skin; and
        at least one second electrode which is disposed in a circumference of the first electrode without being electrically conductive with the first electrode, and which is adapted to be in contact with a skin;
    a microprocessor configured to:
        supply a bipolar stimulation signal between the first electrode and the second electrode, the bipolar stimulation signal including a first waveform signal and a second waveform signal comprising a different amplitude than the first waveform signal, the first waveform signal which is convex in a negative direction in the first electrode, the second waveform signal which is convex in a positive direction in the first electrode, wherein the first waveform signal and the second waveform signal are stimulation waveform signals; and
        change at least one of a voltage and a current of each of the first and second waveform signals to change stimulation intensity in accordance with a user input, wherein,
        by changing the stimulation intensity, nerve fibers to be stimulated can be changed.

2. The pain sensory nerve stimulation apparatus according to claim 1, wherein the microprocessor is further configured to:
    change at least one of a rising time and a falling time of each of the first and second waveform signals.

3. The pain sensory nerve stimulation apparatus according to claim 2, wherein
    at least one of rising and falling of each of the first and second waveform signals is changed so as to have a rectilinear inclined shape.

4. The pain sensory nerve stimulation apparatus according to claim 2, wherein
    at least one of rising and falling of each of the first and second waveform signals is changed so as to have an exponential shape.

5. The pain sensory nerve stimulation apparatus according to claim 1, wherein the microprocessor is further configured to:
    change at least one of a waveform duration, waveform interval, and waveform number of each of the first and second waveform signals.

6. The pain sensory nerve stimulation apparatus according to claim 1, wherein
    in the bipolar stimulation signal, the second waveform signal is supplied after the first waveform signal is supplied, and the first and second waveform signals are connected to each other.

7. The pain sensory nerve stimulation apparatus according to claim 1, wherein
    a peak value of the first waveform signal is different from a peak value of the second waveform signal.

8. The pain sensory nerve stimulation apparatus according to claim 1, wherein
    a peak value of the second waveform signal is higher than a peak value of the first waveform signal.

9. The pain sensory nerve stimulation apparatus according to claim 1, wherein
    the bipolar stimulation signal has a waveform duration of 0.1 to 100 ms.

10. The pain sensory nerve stimulation apparatus according to claim 1, wherein
    a peak value of the second waveform signal is five times or more a peak value of the first waveform signal.

11. The pain sensory nerve stimulation apparatus according to claim 1, wherein
    rising and falling times of the first waveform signal are equal to rising and falling times of the second waveform signal.

12. The pain sensory nerve stimulation apparatus according to claim 1, wherein
    the second electrode is annularly disposed in the circumference of the first electrode.

13. The pain sensory nerve stimulation apparatus according to claim 1, comprising a plurality of the electrode portions.

14. The pain sensory nerve stimulation apparatus according to claim 1, wherein
    the microprocessor is configured to successively supply the bipolar stimulation signal a plurality of times.

15. The pain sensory nerve stimulation apparatus according to claim 1,
    wherein the microprocessor is further configured to stimulate only C fibers of a recipient receiving the stimulation signal by changing at least one of a rising time and a falling time of the bipolar stimulation signal until stimulation of only the C fibers is detected from a patient having the C fibers.

16. The pain sensory nerve stimulation apparatus according to claim 1, wherein,
    by changing the stimulation intensity, Aδ fibers, Aβ fibers and C fibers are stimulated, respectively.

17. The pain sensory nerve stimulation apparatus according to claim 1, wherein,
    in the bipolar stimulation signal, the second waveform signal is supplied after the first waveform signal is supplied, and
    when the bipolar stimulation signal is supplied,
    in the first waveform signal, the first electrode is in the negative side, so that a cathode stimulation is performed, and,
    in the second waveform signal, the first electrode is in the positive side, so that an anode stimulation is performed.

18. The pain sensory nerve stimulation apparatus according to claim 1, wherein
    a peak value of the second waveform signal is higher than a peak value of the first waveform signal,
    in the bipolar stimulation signal, the second waveform signal is supplied after the first waveform signal is supplied, and
    when the bipolar stimulation signal is supplied, in the first waveform signal, the first electrode is in the negative side, so that a cathode stimulation is performed, and, in the second waveform signal, the first electrode is in the positive side, so that an anode stimulation is performed.

19. The pain sensory nerve stimulation apparatus according to claim 1, wherein
a peak value of the second waveform signal is higher than a peak value of the first waveform signal, and
the duration of the second waveform signal is longer than a duration of the first waveform signal.

20. The pain sensory nerve stimulation apparatus according to claim 1, wherein
the first waveform signal which is convex in the negative direction corresponds to a falling edge, the second waveform signal which is convex in the positive direction corresponds to a rising edge in the first electrode.

* * * * *